United States Patent [19]

Day et al.

[11] 4,189,944
[45] Feb. 26, 1980

[54] HYDRODYNAMIC ULTRASONIC PROBE

[75] Inventors: Robert A. Day, Livermore; Armond E. Conti, San Jose, both of Calif.

[73] Assignee: The United States of America as represented by the United States Department of Energy, Washington, D.C.

[21] Appl. No.: 957,620

[22] Filed: Nov. 3, 1978

[51] Int. Cl.$^2$ ............................................. G01N 29/04
[52] U.S. Cl. ........................................................ 73/623
[58] Field of Search ................. 73/623, 633, 634, 638, 73/644

[56] References Cited

U.S. PATENT DOCUMENTS

| | | | |
|---|---|---|---|
| 2,995,925 | 8/1961 | Worlton | 73/623 |
| 3,417,609 | 12/1968 | Grahm | 73/623 |
| 3,810,384 | 5/1974 | Evans | 73/623 |

Primary Examiner—Anthony V. Ciarlante
Attorney, Agent, or Firm—R. V. Lupo; Roger S. Gaither; L. E. Carnahan

[57] ABSTRACT

An improved probe for in-service ultrasonic inspection of long lengths of a workpiece, such as small diameter tubing from the interior. The improved probe utilizes a conventional transducer or transducers configured to inspect the tubing for flaws and/or wall thickness variations. The probe utilizes a hydraulic technique, in place of the conventional mechanical guides or bushings, which allows the probe to move rectilinearly or rotationally while preventing cocking thereof in the tube and provides damping vibration of the probe. The probe thus has lower friction and higher inspection speed than presently known probes.

3 Claims, 3 Drawing Figures

4,189,944

HYDRODYNAMIC ULTRASONIC PROBE

BACKGROUND OF THE INVENTION

The invention described herein was made in the course of, or under, Contract No. E(04-3)-893, Task 10, between the General Electric Company and the United States Department of Energy.

This invention relates to nondestructive testers for inspecting elongated hollow objects, such as pipes, tubes, etc. particularly to ultrasonic testers for tubing, and more particularly to a hydrodynamic ultrasonic probe utilized in such tubing testers.

Steam generator tubing or similar structures often require periodic inspection to assess the integrity of the tubing for continued service. The most sensitive method for such inspection or testing is the ultrasonic method.

The use of ultrasonic waves to detect flaws within objects is well known whereby a pulse of acoustical energy is directed toward the object. A certain amount of the energy will be reflected back by the surface of the object while some of it will be transmitted into the interior. If, for example, a flaw, such as a void in the material is present, a certain portion of the energy will be reflected therefrom along the normal to the surface at a later point in time than that reflected from the surface.

The ultrasonic method of inspecting tubing walls, for example, requires that a probe containing one or more transducers be inserted into the inside of the tube since access to the outside is often difficult or impossible. The ultrasonic probe must be maintained in an accurate location in the tube because of the high index of refraction of sound in metals. Various methods for maintaining the probe position in the tube have been developed. For example, U.S. Pat. No. 2,995,925 to D. C. Worlton utilizes nylon bearings; U.S. Pat. No. 3,417,609 to R. L. Graham utilizes resilient members; U.S. Pat. No. 3,583,211 to K. H. Brech et al utilizes radial projections; while U.S. Pat. No. 3,810,384 to D. J. Evans utilizes resilient cups.

The use of probe guides which contact the tube inner wall results in high friction and can burnish the wall of the tube. Small bumps, such as caused by scale or oxides, on the inner wall surface of the tube cause vibration of the probe when contacted by the guides and limits the translation and rotation speed of the probe. For example, in steam generator tubing, using the prior known probes, inspection requires over an hour per 21 meter long tube, which is very time consuming when a large number of tubes are involved. Thus, a need exists in the ultrasonic tube inspection field for a probe which reduces friction, eliminates vibration problems, and will not burnish the inner wall of the tube.

SUMMARY OF THE INVENTION

The present invention provides a probe for ultrasonic tube inspection systems which fills the above-mentioned need in the prior art. The probe of this invention provides both lower friction and higher inspection speed, thus greatly reducing the problems associated with surface friction and the associated costs of inspection time. The probe of this invention utilizes a hydraulic technique, rather than mechanical guides or bushings, to maintain the probe location. The hydrodynamic ultrasonic probe of this invention allows for rectilinear and rotational movement of the probe while preventing cocking thereof in the tube and damping vibration of the probe.

Therefore, it is an object of the invention to provide an improved ultrasonic probe for inspection of workpieces, such as tubes, pipes, etc.

A further object of the invention is to provide a hydrodynamic ultrasonic probe which reduces friction and increases inspection speed of tubes, etc.

Another object of the invention is to provide an ultrasonic tube inspection probe which utilizes a hydraulic approach for maintaining the probe in proper position within the tube.

Another object of the invention is to provide an ultrasonic probe for tube, etc. inspection which allows the probe to be maintained in the center of the tube while translated or rotated without physically touching the inside of the tube.

Other objects of the invention will become readily apparent to those skilled in the art from the following description and accompanying drawings.

DETAILED DESCRIPTION OF THE PREFERRED EMBODIMENT

The invention involves an improved probe for in-service ultrasonic inspection of workpieces, such as long lengths of small diameter tubing from the inside of the tubing. The hydrodynamic probe of this invention utilizes one or more conventional transducers configured to inspect the tubing of interest for flaws and/or wall thickness variations. The probe uses a hydraulic technique, rather than conventional mechanical guides or bushings, which allows the probe to move rectilinearly or rotationally while preventing cocking of the probe in the tube, and provides for damping vibration of the probe. The probe provides lower friction and higher inspection speed over the prior known ultrasonic inspection probes.

Prior to describing in detail the improved probe of this invention, it is pointed out that ultrasonic inspection apparatus which is utilized with the probe of this invention, and techniques for inspecting tubing, etc., are well known in the art, as evidenced by the above-cited U.S. patents. Thus, details of the transducer, circuitry, etc. necessary for operation of the probe of this invention are well known in the art. Therefore, description of such herein is not deemed necessary to enable one of ordinary skill in the art to utilize the improved ultrasonic inspection probe of this invention.

Figure 1:
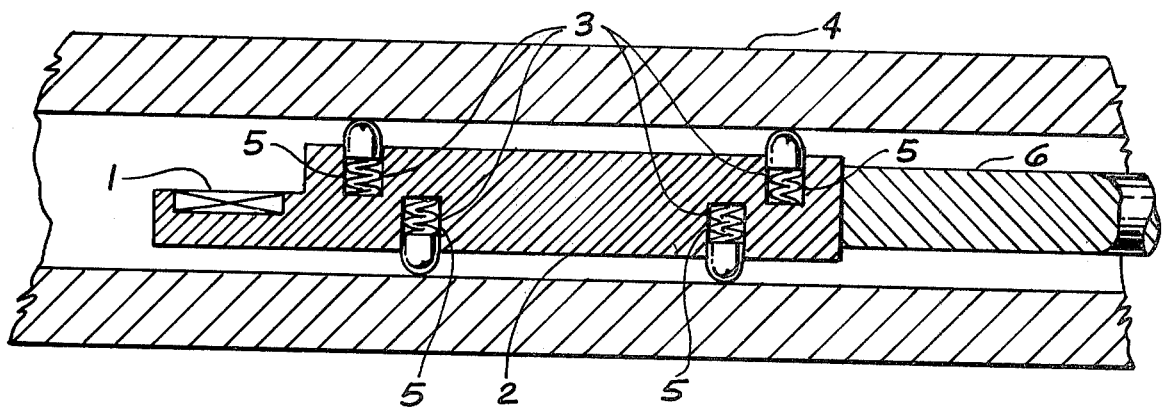
FIG. 1 is a cross-sectional view of a typical prior art ultrasonic probe used in the inspection of tubing, etc.

FIG. 1 illustrates a typical prior art probe which basically consists of an ultrasonic transducer 1 positioned in a probe body 2 which is positioned by spring supported guides, generally indicated at 3, within a tube 4 to be inspected. Spring supported guides 3 are located within countersinks 5 in body 2, with body 2 being secured to a support member 6 as known in the art. It is readily seen that in FIG. 1, as the probe body 2 is moved along the length of the tube 4, or rotated therein, the spring supported guides 3 function to retain it in the center of the tube. The guides 3 produce friction against the inner wall surface of tube 4, and can cause burnishing of the tube surface if not freely movable at all times. It is readily seen that small bumps, usually scale or oxides, on the inner surface of tube 4 increases the friction between the surface and the guides 3, causes vibration of the probe, and limits the translation and rotation speed of the probe.

Figure 2:
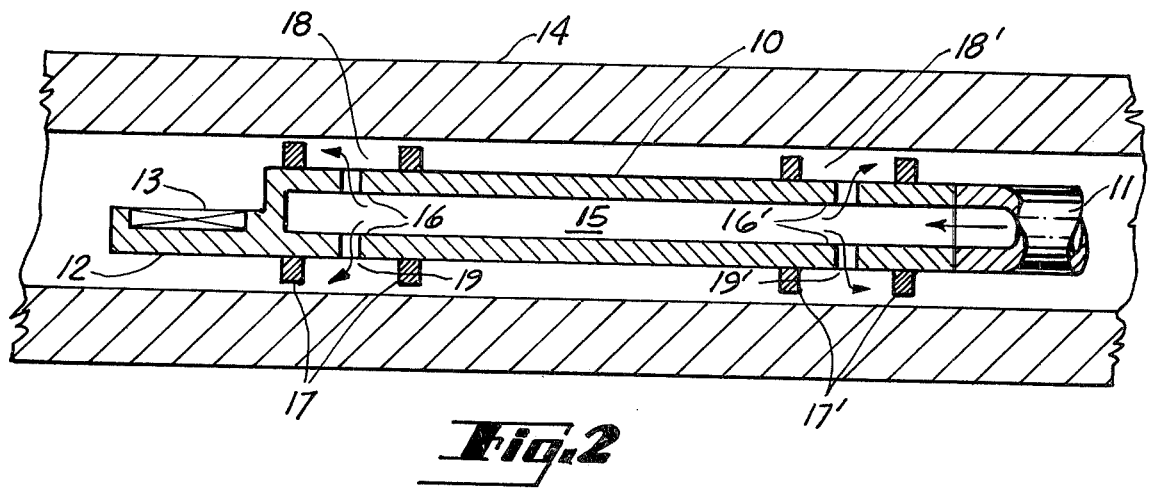
FIG. 2 is a cross-sectional view of an embodiment of the hydrodynamic ultrasonic probe of the invention.

FIG. 2 illustrates an embodiment of the hydrodynamic ultrasonic probe of the invention, which results in lower friction and higher inspection speed over the mechanical guide type probes. As shown, the embodiment consists of a longitudinal probe body 10 secured at one end to a hollow member 11 and provided at the opposite end with a protruding section 12 which supports a transducer 13 of the type conventionally known in the art. Probe body 10 is located within a tube or pipe 14 and is provided with a longitudinally extending cavity or chamber 15 in fluid communication with hollow member 11 and with a plurality of spaced sets of relief holes or apertures 16 and 16' (two sets shown this embodiment) which provide fluid communication from chamber 15 to the exterior of probe body 10. Two pair of spaced outwardly extending flexible glands or members 17 are secured about probe body 10 at opposite ends thereof so as to define an annulus 18 and 18' surrounding the probe body, with holes 16 and 16', respectively, therebetween, which acts as a plenum.

Figure 3:
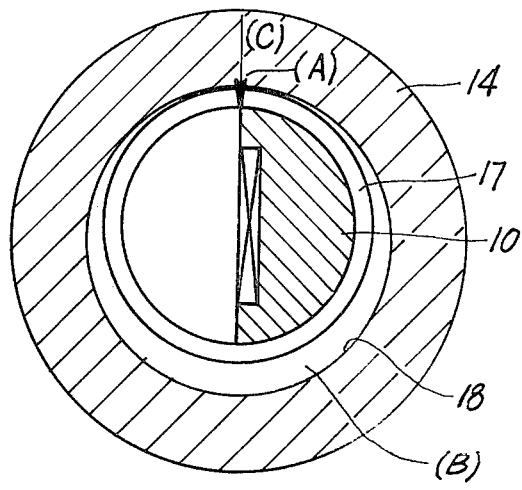
FIG. 3 is a view illustrating the fluid forces which tend to retain the probe in the center of a tube being inspected.

In operation of the FIG. 2 embodiment, as illustrated in FIGS. 2 and 3, fluid, such as water, under pressure is pumped from a source, not shown, through hollow member 11 and into the chamber or cavity 15 of probe body 10 as indicated by the flow arrows. The fluid flows into cavity 15 and into annulus 18, as indicated by arrows 19, and the pressure is sufficient to allow the fluid to build up a pressure between the flexible glands 17. The fluid flow must be sufficient to allow the flow through the relief holes 16 to exceed that which passes around the periphery of the glands 17 such that a position pressure is maintained in the annulus 18. This keeps the probe body 10 centered in tube 14. If the probe is moved from the center of tube 14 (see FIG. 3), then the spacing between the glands 17 and the inner surface of tube 14 is reduced on one side, as indicated at (A), increasing the pressure on that side of the probe body and the fluid flow is increased on the other side of the probe, as indicated at (B), reducing the pressure on that (A) side of the probe. This creates a restoring force, indicated by the arrow (C), which tends to return the probe to the center of tube 14, as shown in FIG. 2. The greater movement of probe body 10 from the center of tube 14, the greater the restoring force (C). This allows the probe to be maintained in the center of the tube while translated or rotated without physically touching the inner surface of the tube. It is thus readily apparent that the principal advantages of the improved probe is reduced friction and reduced risk of scratching or burnishing the inner surface of the tube. Thus, the speed at which the probe can be translated or rotated will, as a consequence of the reduced friction, be increased substantially.

By way of example, to examine a tube having an internal diameter of 1 cm, the probe body 10 would be constructed of stainless steel or other material compatible with the working fluid having an external diameter of 0.82 cm, with the holes 16 and 16' having a diameter of 1 mm and spaced 30° apart, and cavity 15 having a length of approximately 4 cm and diameter of 0.6 cm. The flexible glands 17 and 17' may be constructed of nylon or neoprene having an outer diameter of 0.98 cm and thickness of 1 mm, such that an opening of about 0.02 cm minimum normally exists between the periphery of the glands and the inner surface of the tube when the probe is centered in the tube. Fluid under pressure of 0.25 to 1.0 megapascals is directed via hollow member 11 into cavity or chamber 15, with a positive pressure, under probe centered conditions, of 0.2 to 0.8 megapascals in annuli 18 and 18'.

As pointed out above, inspection time of steam generator tubing using the prior art mechanically guided probes requires over one hour to inspect a tube 21 meters long. Because of the reduced friction between the probe and the tube provided by the hydrodynamic probe of this invention, the examination time of such a 21 meter long tube would be 15 min. This results in a substantial decrease in overall time of inspection, particularly when the large number of such tubes used in steam generators is considered.

It has thus been shown that the present invention provides an improved probe for ultrasonic testing or inspection of workpieces, such as tubing, pipes, etc., which greatly increases the speed of inspection due to the decreased friction of the probe within the tube or pipe. The hydraulic centering technique of the probe of this invention allows the probe to move rectilinearly or rotationally while preventing cocking of the probe in the tube and damping vibration of the probe. The probe of this invention also reduces the risk of scratching or burnishing the inner surface of the tube being examined.

While a particular embodiment of the invention has been illustrated and described, modifications will become apparent to those skilled in the art, and it is intended to cover in the appended claims all such modifications as come within the spirit and scope of the invention.

What we claim is:

1. In an ultrasonic unit for inspecting an elongated hollow workpiece for wall thickness and flaws, the improvement comprising a hydrodynamic probe; said probe comprising a longitudinally extending cylindrical body member having a cavity extending longitudinally therein and adapted to be connected with an associated pressurized fluid source, said body member being provided with a plurality of sets of longitudinally spaced holes defining fluid passages between said cavity and an outer surface of said body member, and at least two pair of radially outwardly extending flexible members secured in spaced relation about said outer surface of said body member, each of said pair of flexible members being positioned such that at least one set of said plurality of sets of spaced holes is located therebetween with respect to said outer surface of said body member, each pair of flexible members defining an annulus therebetween, whereby when said body member is inserted into an associated hollow workpiece to be inspected and fluid under pressure is directed into said cavity and outwardly through said spaced holes, each of said annulus functions as a fluid pressure plenum with respect to such an associated workpiece to maintain said body member centrally located within such an associated workpiece.

2. The improved probe defined in claim 1, wherein said body member additionally includes a longitudinally extending section adapted to retain thereon an associated ultrasonic transducer.

3. The improved probe defined in claim 1, wherein said plurality of sets of longitudinally spaced holes consists of two sets having annularly spaced holes.

* * * * *